(12) United States Patent
Tanigawa et al.

(10) Patent No.: US 8,096,950 B2
(45) Date of Patent: Jan. 17, 2012

(54) IMAGE PROCESSING APPARATUS AND ULTRASONIC DIAGNOSTIC APPARATUS

(75) Inventors: Shunichiro Tanigawa, Tokyo (JP); Koji Miyama, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 662 days.

(21) Appl. No.: 12/188,112

(22) Filed: Aug. 7, 2008

(65) Prior Publication Data

US 2009/0043201 A1    Feb. 12, 2009

(30) Foreign Application Priority Data

Aug. 9, 2007    (JP) ................. 2007-207329

(51) Int. Cl.
*A61B 8/00* (2006.01)
(52) U.S. Cl. .......... 600/443; 600/407; 600/437
(58) Field of Classification Search .......... 600/407, 600/437, 444, 443, 447; 382/128
See application file for complete search history.

(56) References Cited

U.S. PATENT DOCUMENTS

| | | |
|---|---|---|
| 5,188,113 A | 2/1993 | Sato et al. |
| 5,383,457 A | 1/1995 | Cohen |
| 5,422,827 A | 6/1995 | Niehaus |
| 5,431,169 A | 7/1995 | Gondo |
| 5,503,153 A | 4/1996 | Liu et al. |
| 5,515,849 A | 5/1996 | Murashita et al. |
| 5,551,433 A | 9/1996 | Wright et al. |
| 5,706,818 A | 1/1998 | Gondo |
| 5,798,461 A | 8/1998 | Banta, Jr. et al. |
| 6,843,770 B2 | 1/2005 | Sumanaweera |
| 2002/0000988 A1* | 1/2002 | Nelson et al. ............. 345/443 |
| 2007/0053566 A1 | 3/2007 | Kim et al. |
| 2007/0160145 A1* | 7/2007 | Kwon et al. ......... 375/240.16 |

FOREIGN PATENT DOCUMENTS

| | | |
|---|---|---|
| JP | 07-044701 | 2/1995 |
| JP | 09-220228 | 8/1997 |

* cited by examiner

*Primary Examiner* — Tse Chen
*Assistant Examiner* — Joel F Brutus
(74) *Attorney, Agent, or Firm* — Armstrong Teasdale LLP

(57) ABSTRACT

An image processing apparatus includes a random processing device which adds independent random components to a pixel value of a pixel point on each actual frame corresponding to a given time and a pixel value of a pixel point on each actual frame corresponding to a time subsequent to the time respectively thereby to obtain random-processed pixel values and a weighting/adding device which weights/adds the random-processed pixel values thereby to obtain a pixel value of a pixel point on each interpolation frame corresponding to an intermediate time.

17 Claims, 4 Drawing Sheets

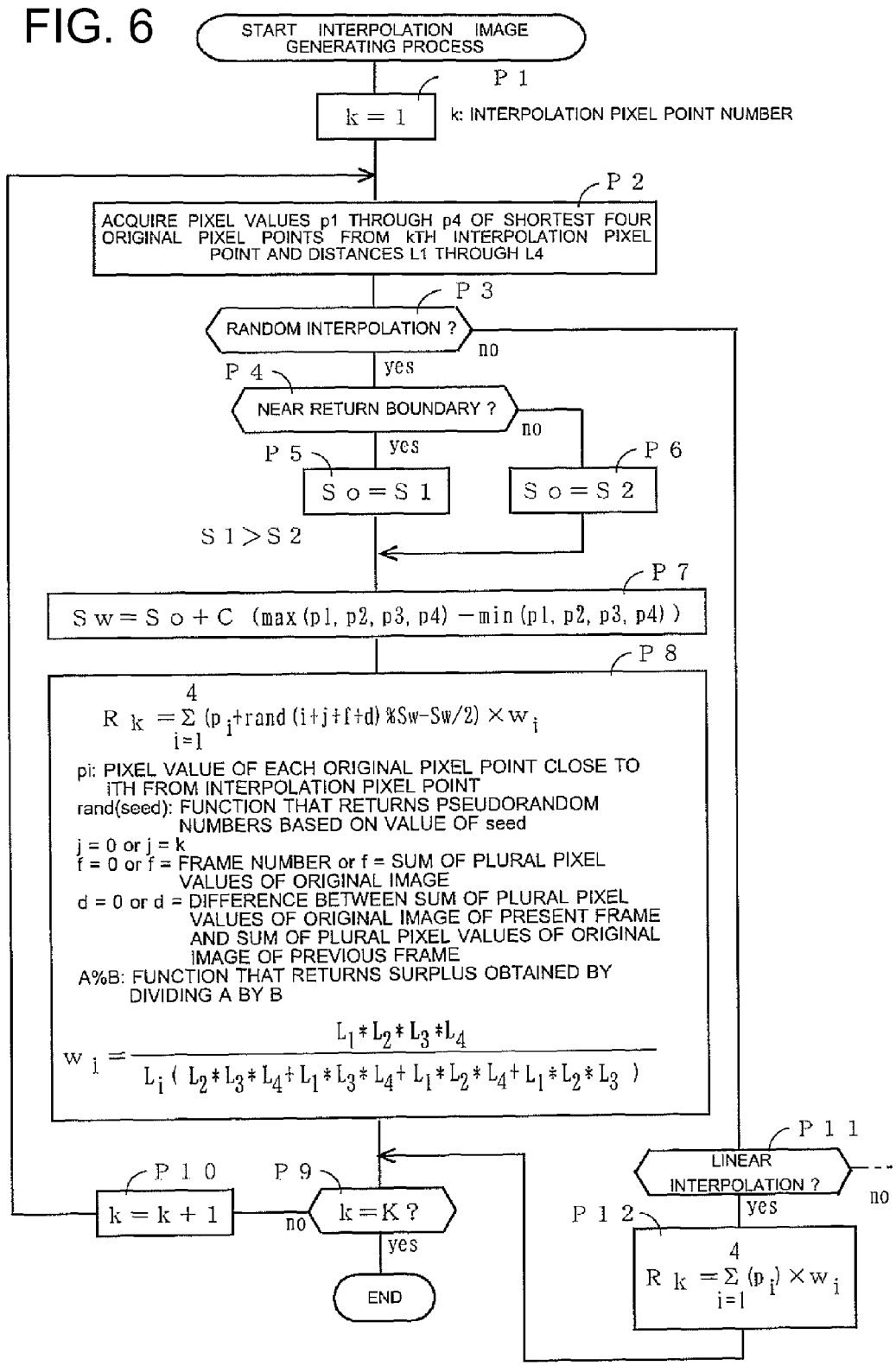

IMAGE PROCESSING APPARATUS AND ULTRASONIC DIAGNOSTIC APPARATUS

CROSS REFERENCE TO RELATED APPLICATIONS

This application claims the benefit of Japanese Patent Application No. 2007-207329 filed Aug. 9, 2007, which is hereby incorporated by reference in its entirety.

BACKGROUND OF THE INVENTION

The subject matter disclosed herein relates to an image processing apparatus and an ultrasonic diagnostic apparatus, and more specifically to an image processing apparatus and an ultrasonic diagnostic apparatus capable of generating more natural-looking interpolation frames.

There has heretofore been known an ultrasonic diagnostic apparatus wherein a pixel value of a pixel point on each actual frame (a frame in which each pixel value is obtained by actual measurement) corresponding to a given time and a pixel value of a pixel point on each actual frame corresponding to a time subsequent to the time are weighted/added to obtain a pixel value of a pixel point on each interpolation frame (a frame in which each pixel value is obtained by interpolation calculation) corresponding to an intermediate time (refer to, for example, Japanese Unexamined Patent Publication No. Hei 9(1997)-220228).

On the other hand, there has been known an image processing apparatus wherein on an actual frame, each pixel value is calculated by linear interpolation from pixel values of a plurality of original pixel points (pixel points at which pixel values are obtained by actual measurement) in the neighborhood of each interpolation pixel point (a pixel point at which each pixel value is obtained by interpolation calculation), and each of random components is added to the calculated pixel value thereby to obtain a pixel value of each interpolation pixel point (refer to, for example, Japanese Unexamined Patent Publication No. Hei 7(1995)-44701).

If the two prior arts are combined into one, it is then considered that the pixel value of the pixel point on each actual frame corresponding to the given time and the pixel value of the pixel point on each actual frame corresponding to its subsequent time are weighted/added, and each random component is added to the pixel value obtained by weighting/adding to obtain the pixel value of the pixel point on each interpolation frame corresponding to the intermediate time.

Thus, each random component is added to the pixel value calculated by linear interpolation to obtain the pixel value of the pixel point on each interpolation frame, thereby making it possible to create the intended interpolation frame that is naturally seen as compared with such a case that the pixel value calculated by linear interpolation is set as the pixel value of the pixel point on the interpolation frame as it is.

A problem, however, arises in that since the degree of freedom of each added random component is 1, a natural-looking degree becomes insufficient.

BRIEF DESCRIPTION OF THE INVENTION

It is desirable that the problem described previously is solved.

In a first aspect, the invention provides an image processing apparatus including a random processing device which adds independent random components to a pixel value of a pixel point on each actual frame corresponding to a given time and a pixel value of a pixel point on each actual frame corresponding to a time subsequent to the time respectively thereby to obtain random-processed pixel values, and a weighting/adding device which weights/adds the random-processed pixel values thereby to obtain a pixel value of a pixel point on each interpolation frame corresponding to an intermediate time.

In the image processing apparatus according to the first aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components reaches 2 and a natural-looking degree can hence be enhanced.

In a second aspect, the invention provides an image processing apparatus wherein in the image processing apparatus according to the first aspect, a pixel value rk (where k=1, 2, 3, ..., K) of each interpolation pixel point is determined from the following equation:

$$rk = \sum_{i=1}^{2} (p(t_i) + rand(i) \% \ Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, A % B is a function that returns the surplus obtained by dividing A by B, Sw is a designated value of random strength, and wi is a weighting/adding weight.

In the image processing apparatus according to the second aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components reaches 2 and a natural-looking degree can hence be enhanced.

In a third aspect, the invention provides an image processing apparatus wherein in the image processing apparatus according to the first aspect, a pixel value rk (where k=1, 2, 3, ..., K) of each interpolation pixel point is determined from the following equation:

$$rk = \sum_{i=1}^{2} (p(t_i) + rand(i+k) \% \ Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, A % B is a function that returns the surplus obtained by dividing A by B, Sw is a designated value of random strength, and wi is a weighting/adding weight.

In the image processing apparatus according to the third aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components becomes 2 and a natural-looking degree can hence be enhanced.

Since random components different every interpolation pixel point are provided, the appearance of regular patterns on each image can be suppressed even in this respect, and thereby a natural-looking degree can be enhanced.

In a fourth aspect, the invention provides an image processing apparatus wherein in the image processing apparatus according to the first aspect, a pixel value rk (where k=1, 2, 3, . . . , K) of each interpolation pixel point is determined from the following equation:

$$rk = \sum_{i=1}^{2} (p(t_i) + rand(i+f) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, f is a serial number of each interpolation frame or sum of pixel values of a plurality of pixel points on each actual frame immediately before or immediately after each interpolation frame, A % B is a function that returns the surplus obtained by dividing A by B, Sw is a designated value of random strength, and wi is a weighting/adding weight.

In the image processing apparatus according to the fourth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components becomes 2 and a natural-looking degree can hence be enhanced.

Since random components different every interpolation frame are provided, the appearance of regular patterns in a time direction can be suppressed, and the degree that the corresponding frame is naturally seen as a moving picture or image can hence be enhanced.

In a fifth aspect, the invention provides an image processing apparatus wherein in the image processing apparatus according to the first aspect, a pixel value rk (where k=1, 2, 3, . . . , K) of each interpolation pixel point is determined from the following equation:

$$rk = \sum_{i=1}^{2} (p(t_i) + rand(i+d) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, d is a difference between sum of pixel values of a plurality of pixel points on each actual frame immediately before each interpolation frame and sum of pixel values of a plurality of pixel points on each actual frame immediately after each interpolation frame, A % B is a function that returns the surplus obtained by dividing A by B, Sw is a designated value of random strength, and wi is a weighting/adding weight.

In the image processing apparatus according to the fifth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components becomes 2 and a natural-looking degree can hence be enhanced.

Since random components different according to time-dependent changes of actual frame are added or provided, the appearance of regular patterns can be suppressed, and the degree that the corresponding frame is naturally seen as a moving picture or image can hence be enhanced.

In a sixth aspect, the invention provides an image processing apparatus wherein in the image processing apparatus according to the first aspect, a pixel value rk (where k=1, 2, 3, . . . , K) of each interpolation pixel point is determined from the following equation:

$$rk = \sum_{i=1}^{2} (p(t_i) + rand(i+j+f+d) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, j=0 or j=k, f=0 or is a sum of pixel values of a plurality of pixel points on serial number of each interpolation frame or each actual frame immediately before or immediately after each interpolation frame, d=0 or is a difference between sum of pixel values of a plurality of pixel points on each actual frame immediately before each interpolation frame and sum of pixel values of a plurality of pixel points on each actual frame immediately after each interpolation frame, and A % B is a function that returns the surplus obtained by dividing A by B.

In the image processing apparatus according to the sixth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components becomes 2 and a natural-looking degree can hence be enhanced.

It is possible to add or provide random components different every interpolation pixel point, provide random components different every interpolation frame and provide random components different according to time-dependent changes of actual frame. Therefore, the appearance of regular patterns can be suppressed and a natural-looking degree can hence be enhanced.

In a seventh aspect, the invention provides an image processing apparatus wherein in the image processing apparatus according to any one of the second through sixth aspects, a device is provided which determines a designated value Sw of random strength from the following equation:

$$Sw = So + C(\max\{p(t1), p(t2)\} - \min\{p(t1), p(t2)\})$$

where So is a standard value, C is an adjustment coefficient, max(p(t1),p(t2) is a function that returns the maximum value of p(t1) and p(t2), and min(p(t1),p(t2) is a function that returns the minimum value of p(t1) and p(t2).

In the image processing apparatus according to the seventh aspect, larger random components can be added as the difference between pixel values of pixel points on actual frames becomes large. It is therefore possible to enhance a natural-looking degree.

In an eighth aspect, the invention provides an image processing apparatus wherein in the image processing apparatus according to any one of the second through seventh aspects, a device is provided which determines a weighting/adding weight wi from the following equation:

$$w_1 = \frac{Tb}{Ta+Tb} w_2 = \frac{Ta}{Ta+Tb}$$

where Ta is a time difference between actual frame immediately before interpolation frame and interpolation frame, and Tb is a time difference between actual frame immediately after interpolation frame and interpolation frame.

In the image processing apparatus according to the eighth aspect, so long as an actual frame close to an interpolation frame is taken, the contribution of its pixel value can be made greater.

In a ninth aspect, the invention provides an ultrasonic diagnostic apparatus including an ultrasonic scan device which scans a subject by ultrasound to obtain time-series actual frames, a random processing device which adds independent random components to a pixel value of a pixel point on each actual frame corresponding to a given time and a pixel value of each original pixel point on each actual frame corresponding to a time subsequent to the time respectively thereby to obtain random-processed pixel values, a weighting/adding device which weights/adds the random-processed pixel values thereby to obtain a pixel value of a pixel point on each interpolation frame corresponding to an intermediate time, and an image display device which displays the interpolation frame.

In the ultrasonic diagnostic apparatus according to the ninth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components becomes 2 and a natural-looking degree can hence be enhanced.

In a tenth aspect, the invention provides an ultrasonic diagnostic apparatus wherein in the ultrasonic diagnostic apparatus according to the ninth aspect, a pixel value rk (where k=1, 2, 3, . . . , K) of each interpolation pixel point is determined from the following equation:

$$rk = \sum_{i=1}^{2} (p(t_i) + rand(i) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, A % B is a function that returns the surplus obtained by dividing A by B, Sw is a designated value of random strength, and wi is a weighting/adding weight.

In the ultrasonic diagnostic apparatus according to the tenth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components becomes 2 and a natural-looking degree can hence be enhanced.

In an eleventh aspect, the invention provides an ultrasonic diagnostic apparatus wherein in the ultrasonic diagnostic apparatus according to the ninth aspect, a pixel value rk (where k=1, 2, 3, . . . , K) of each interpolation pixel point is determined from the following equation:

$$rk = \sum_{i=1}^{2} (p(t_i) + rand(i+k) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, A %

B is a function that returns the surplus obtained by dividing A by B, Sw is a designated value of random strength, and wi is a weighting/adding weight.

In the ultrasonic diagnostic apparatus according to the eleventh aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components becomes 2 and a natural-looking degree can hence be enhanced.

Since random components different every interpolation pixel point are provided, the appearance of regular patterns in a time direction can be suppressed, and the degree that the corresponding frame is naturally seen as a moving picture or image can hence be enhanced.

In a twelfth aspect, the invention provides an ultrasonic diagnostic apparatus wherein in the ultrasonic diagnostic apparatus according to the ninth aspect, a pixel value rk (where k=1, 2, 3, . . . , K) of each interpolation pixel point is determined from the following equation:

$$rk = \sum_{i=1}^{2}(p(t_i) + rand(i+f) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, f is a serial number of each interpolation frame or sum of pixel values of a plurality of pixel points on each actual frame immediately before or immediately after each interpolation frame, A % B is a function that returns the surplus obtained by dividing A by B, Sw is a designated value of random strength, and wi is a weighting/adding weight.

In the ultrasonic diagnostic apparatus according to the twelfth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components reaches 2 and a natural-looking degree can hence be enhanced.

Since random components different every interpolation frame are provided, the appearance of regular patterns can be suppressed and a natural-looking degree can hence be enhanced.

In a thirteenth aspect, the invention provides an ultrasonic diagnostic apparatus wherein in the ultrasonic diagnostic apparatus according to the ninth aspect, a pixel value rk (where k=1, 2, 3, . . . , K) of each interpolation pixel point is determined from the following equation:

$$rk = \sum_{i=1}^{2}(p(t_i) + rand(i+d) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, d is a difference between sum of pixel values of a plurality of pixel points oil each actual frame immediately before each interpolation frame and sum of pixel values of a plurality of pixel points on each actual frame immediately after each interpolation frame, A % B is a function that returns the surplus obtained by dividing A by B, Sw is a designated value of random strength, and wi is a weighting/adding weight.

In the ultrasonic diagnostic apparatus according to the thirteenth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components reaches 2 and a natural-looking degree can hence be enhanced.

Since random components different according to time-dependent changes of actual frame are added or provided, the appearance of regular patterns in a time direction can be suppressed, and the degree that the corresponding frame is naturally seen as a moving picture or image can hence be enhanced.

In a fourteenth aspect, the invention provides an ultrasonic diagnostic apparatus wherein in the ultrasonic diagnostic apparatus according to the ninth aspect, a pixel value rk (where k=1, 2, 3, . . . , K) of each interpolation pixel point is determined from the following equation:

$$rk = \sum_{i=1}^{2}(p(t_i) + rand(i+j+f+d) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, j=0 or j=k, f=0 or is a sum of pixel values of a plurality of pixel points on serial number of each interpolation frame or each actual frame immediately before or immediately after each interpolation frame, d=0 or is a difference between sum of pixel values of a plurality of pixel points on each actual frame immediately before each interpolation frame and sum of pixel values of a plurality of pixel points on each actual frame immediately after each interpolation frame, and A % B is a function that returns the surplus obtained by dividing A by B.

In the ultrasonic diagnostic apparatus according to the fourteenth aspect, independent random components are respectively added to pixel values of respective pixel points corresponding to interpolation pixel points on actual frames that interpose interpolation frames therebetween, without adding random components to calculated pixel values and setting the same as pixel values of pixel points on the interpolation frames, thereby to obtain random-processed pixel values. Thereafter, a pixel value obtained by weighting/adding the random-processed pixel values is used as a pixel value of each interpolation pixel point. Therefore, the degree of freedom of the added random components reaches 2 and a natural-looking degree can hence be enhanced.

It is possible to add or provide random components different every interpolation pixel point, provide random components different every interpolation frame and provide random components different according to time-dependent changes of actual frame. Therefore, the appearance of regular patterns can be suppressed and a natural-looking degree can hence be enhanced.

In a fifteenth aspect, the invention provides an ultrasonic diagnostic apparatus wherein in the ultrasonic diagnostic apparatus according to any of the ninth to fourteenth aspects, a device is provided which determines a designated value Sw of random strength from the following equation:

$$Sw = So + C(\max\{p(t1), p(t2)\} - \min\{p(t1), p(t2)\})$$

where So is a standard value, C is a adjustment coefficient, $\max(p(t1), p(t2))$ is a function that returns the maximum value of $p(t1)$ and $p(t2)$, and $\max(p(t1), p(t2))$ is a function that returns the minimum value of $p(t1)$ and $p(t2)$.

In the image processing apparatus according to the fifteenth aspect, a natural-looking degree can be enhanced since larger random components can be added as the difference between pixel values of pixel points on actual frames becomes large.

In a sixteenth aspect, the invention provides an ultrasonic diagnostic apparatus wherein in the ultrasonic diagnostic apparatus according to any of the ninth to fourteenth aspects, a device which determines whether the position of each interpolation pixel point is in the neighborhood of a return or turn-back region, and a device which determines the designated value Sw of random strength in such a manner that the designated value Sw becomes greater than that at other position at the position in the neighborhood of the turn-back region, are provided.

In the above construction, the "turn-back region" means a region in which when the original pixel value is larger than an upper limit of a pixel value or smaller than a lower limit thereof, an apparent pixel value assumes such a value that it is turned back from the upper limit to the lower limit or such a value that it is turned back from the lower limit to the upper limit.

In the ultrasonic diagnostic apparatus according to the sixteenth aspect, a natural-looking degree can be enhanced since random components larger than the others can be added in the neighborhood of an unnaturally easy-to-see turn-back region.

In a seventeenth aspect, the invention provides an ultrasonic diagnostic apparatus wherein in the ultrasonic diagnostic apparatus according to any of the ninth to sixteenth aspects, a device is provided which determines a weighting/adding weight wi from the following equation:

$$w_1 = \frac{Tb}{Ta+Tb} w_2 = \frac{Ta}{Ta+Tb}$$

where Ta is a time difference between actual frame immediately before interpolation frame and interpolation frame, and Tb is a time difference between actual frame immediately after interpolation frame and interpolation frame.

In the ultrasonic diagnostic apparatus according to the seventeenth aspect, so long as an actual frame close to an interpolation frame is taken, the contribution of its pixel value can be made greater.

According to an image processing apparatus and an ultrasonic diagnostic apparatus of the invention, natural-looking interpolation frames can be created.

An image processing apparatus and an ultrasonic diagnostic apparatus according to the invention can be used to create natural-looking interpolation frames.

Further objects and advantages of the present invention will be apparent from the following description of the preferred embodiments of the invention as illustrated in the accompanying drawings.

BRIEF DESCRIPTION OF THE DRAWINGS

FIG. 6 is a flowchart showing an interpolation image generating process using the ultrasonic diagnostic apparatus shown in FIG. 4.

DETAILED DESCRIPTION OF THE INVENTION

The invention will hereinafter be explained in further detail in accordance with embodiments illustrated in the accompanying drawings. Incidentally, the invention is not limited thereby.

Figure 1:
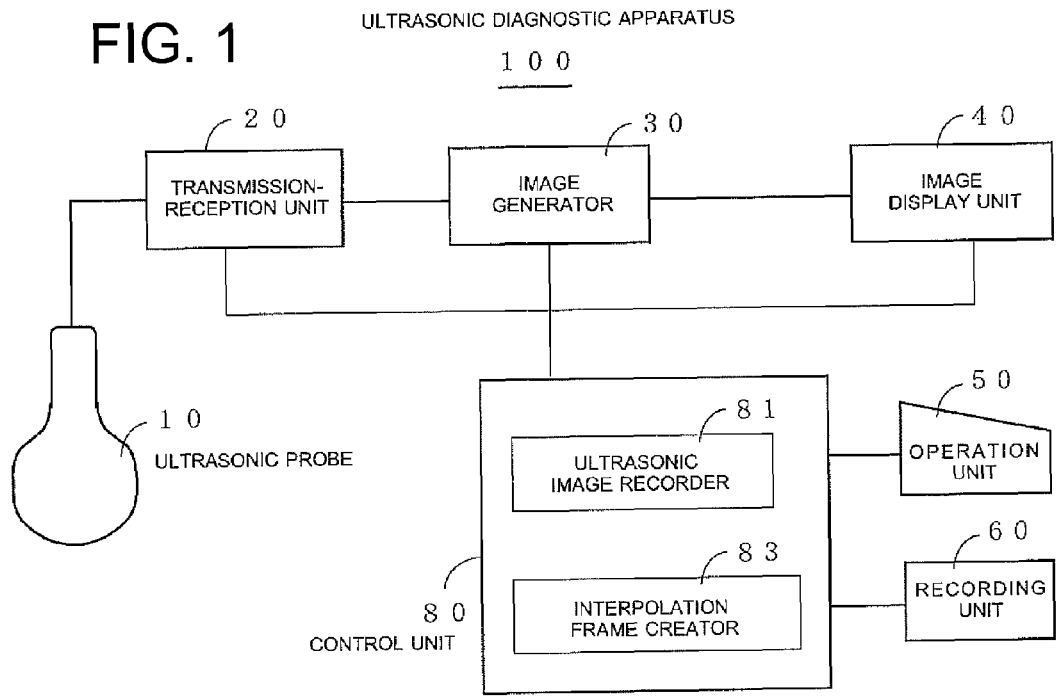
FIG. 1 is a block diagram showing an exemplary ultrasonic diagnostic apparatus.

FIG. 1 is a construction block diagram of an ultrasonic diagnostic apparatus 100 according to an embodiment 1.

The ultrasonic diagnostic apparatus 100 includes an ultrasonic probe 10, a transmission-reception unit 20 which drives the ultrasonic probe 10 to scan within a subject with an ultrasonic beam, an image generator 30 which generates each of a time series of ultrasonic images (actual frames), based on a signal obtained by the transmission-reception unit 20, an image display unit 40 which displays the ultrasonic image and an interpolation image (interpolation frame) or the like produced based on it, an operation or control unit 50 for giving instructions and data by an operator, a recording unit 60 which records the ultrasonic image or the like therein, a control unit 80 which controls the whole, and an ultrasonic image recorder 81 and an interpolation frame creator 83 both included in the control unit 80.

Figure 2:
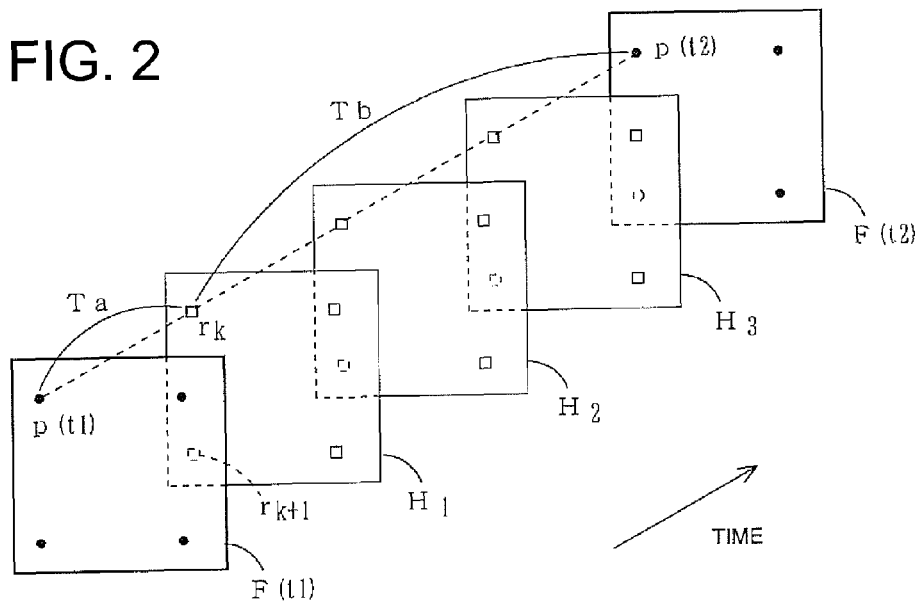
FIG. 2 is a conceptual diagram illustrating interpolation frames and actual frames.

FIG. 2 is an explanatory diagram showing actual frames and interpolation frames.

An actual frame F(t1) is an ultrasonic image obtained by a scan corresponding to a time t1. An actual frame F(t2) is an ultrasonic image obtained by a scan corresponding to a time t2 subsequent to the time t1.

An interpolation frame HI is an interpolation image corresponding to a time "t1+Ta" set between the time t1 and the time t2.

A pixel value rk (assume that rk indicates both an interpolation pixel point and its pixel value) of an interpolation pixel point rk placed on the interpolation frame H1 corresponding to the time "t1+Ta" is determined by calculation from a pixel value p(t1) (assumes that p(t1) indicates both a pixel point and its pixel value) of a pixel point p(t1) corresponding to the interpolation pixel point rk, which is placed on the actual frame F(t1) lying immediately before the time "t1+Ta", and a pixel value p(t2) (assumes that p(t2) indicates both a pixel point and its pixel value) of a pixel point p(t2) corresponding to the interpolation pixel point rk, which is placed on the actual frame F(t2) lying immediately after the time "t1+Ta".

In a manner similar to the interpolation frame H1, interpolation frames H2 and H3 are also obtained by calculations based on the actual frame F(t1) and the actual frame F(t2).

Figure 3:
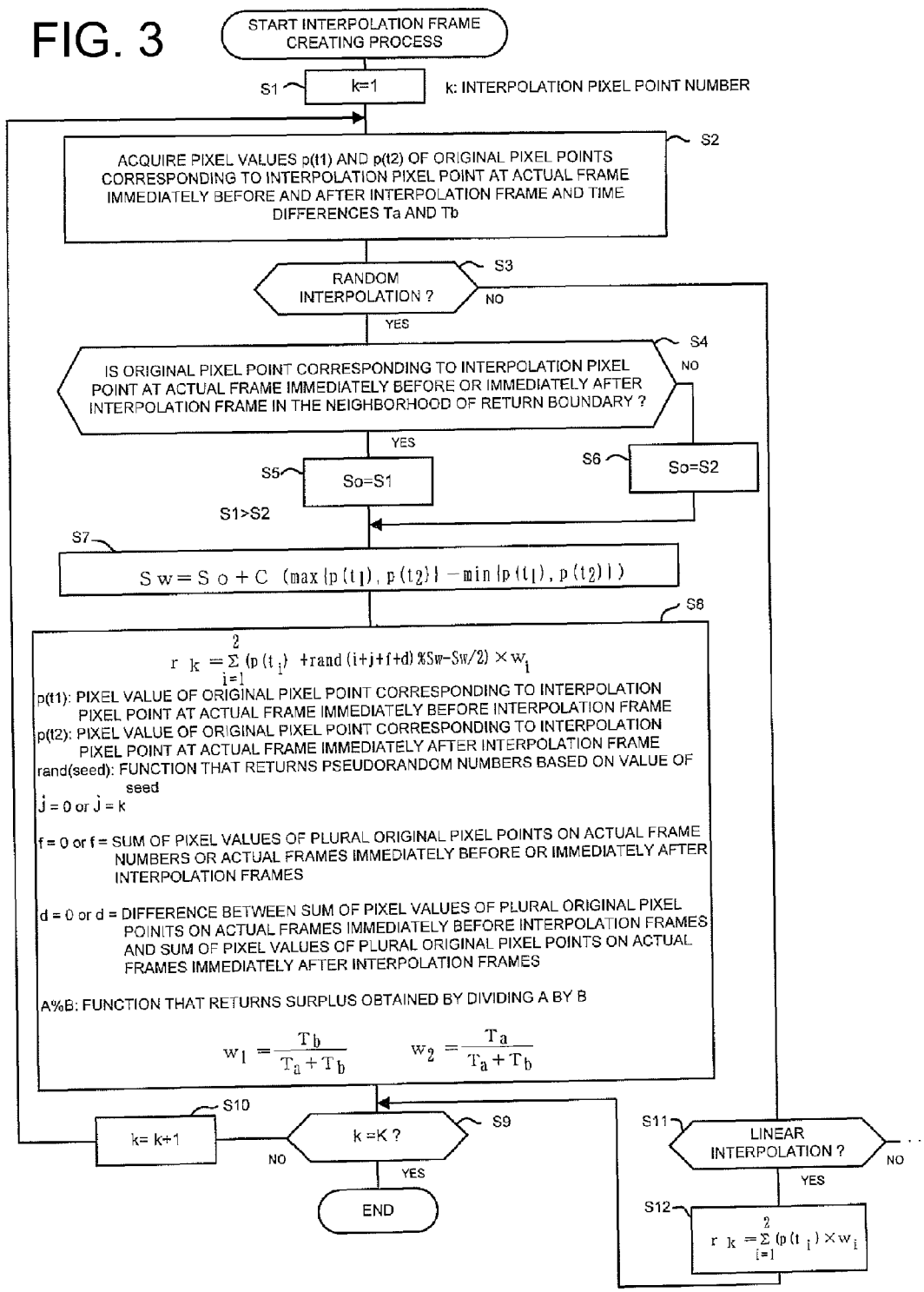
FIG. 3 is a flowchart depicting an interpolation frame creating process using the ultrasonic diagnostic apparatus shown in FIG. 1.

FIG. 3 is a flowchart showing an interpolation frame creating process executed by the interpolation frame creator 83. Incidentally, it will be explained assuming that the interpolation frame H1 is created.

At Step S1, an interpolation pixel point number counter is initialized to k=1. Interpolation pixel point numbers are serial numbers attached to respective pixel points on interpolation frames.

At Step S2 as shown in FIG. 2, a pixel value p(t1) of a pixel point p(t1) corresponding to an interpolation pixel point rk, which is placed on an actual frame F(t1) lying immediately before a time "t1+Ta" corresponding to an interpolation frame H1, a pixel value p(t2) of a pixel point p(t2) corresponding to the interpolation pixel point rk, which is placed on an actual frame F(t2) lying immediately after the time "t1+Ta", a time difference Ta between the interpolation frame H1 and the actual frame F(t1), and a time difference Tb between the interpolation frame H1 and the actual frame F(t2) are acquired.

At Step S3, the interpolation frame creating process proceeds to Step S4 if an operator selects "random interpolation". If not so, then the interpolation frame creating process proceeds to Step S11.

At Step S4, the interpolation frame creating process proceeds to Step S5 if the position of the pixel point p(t1) on the actual frame F(t1) is placed in the neighborhood of a turnback or return region. If the position of the pixel point p(t2) on the actual frame F(t2) is near the return region, then the interpolation frame creating process proceeds to Step S5. If not so, then the interpolation frame creating process proceeds to Step S6.

Assume that the pixel value takes values lying within a range from −128 to 127, for example. When the pixel values of four points closest to the pixel point p(t1) are p1, p2, p3 and p4 respectively, it is determined that they are near the return region where |p1-p2|>127, |p3-p4|>127 or |p1-p3|>127 is satisfied.

At Step S5, a standard value So is defined as So=S1. Then, the interpolation frame creating process proceeds to Step S7.

At Step S6, the standard value So is defined as So=S2. However, S1 and S2 are assumed to be S1>S2. Then, the interpolation frame creating process proceeds to Step S7.

At Step S7, a designated or specified value Sw of random strength is calculated from the following equation:

$$Sw = So + C(\max\{p(t1), p(t2)\} - \min\{p(t1), p(t2)\})$$

where So is a standard value, C is a adjustment coefficient, max(p(t1),p(t2)) is a function that returns the maximum value of p(t1) and p(t2), and min(p(t1),p(t2)) is a function that returns the minimum value of p(t1) and p(t2).

At Step S8, a pixel value rk of each interpolation pixel point is determined from the following equation:

$$rk = \sum_{i=1}^{2} (p(t_i) + rand(i + j + f + d) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(seed) is a function that returns pseudorandom numbers based on value of seed, j=0 or j=k, f=0 or is a sum of pixel values of a plurality of pixel points on serial number of each interpolation frame or each actual frame immediately before or immediately after each interpolation frame, d=0 or is a difference between sum of pixel values of a plurality of pixel points on each actual frame immediately before each interpolation frame and sum of pixel values of a plurality of pixel points on each actual frame immediately after each interpolation frame, and A % B is a function that returns the surplus obtained by dividing A by B.

Here, the operator can select j=0 or j=k. The operator can select either the sum of pixel values in the whole surface or partial region on a frame number (attached to each frame) of f=0 or f=interpolation frame H1, or f=actual frame F(t1) or the sum of pixel values in the whole surface or partial region on f=actual frame F(t2). The operator is able to select the difference between the sum of pixel values in the whole surface or partial region on d=0 or d=actual frame F(t1) and the sum of pixel values in the whole surface or partial region on the actual frame F(t2). A weighting/adding weight wi is calculated from the following equation:

$$w_1 = \frac{Tb}{Ta + Tb} w_2 = \frac{Ta}{Ta + Tb}$$

where Ta is a time difference between actual frame immediately before interpolation frame and interpolation frame, and Tb is a time difference between actual frame immediately after interpolation frame and interpolation frame.

At Step S9, the interpolation frame creating process is terminated when the interpolation pixel point number counter k has reached the final value K. If not so, then the interpolation frame creating process proceeds to Step S10.

At Step S10, the interpolation pixel point number counter k is incremented by 1 and the interpolation frame creating process is returned to Step S2.

At Step S11, the interpolation frame creating process proceeds to Step S12 when the operator has selected linear interpolation. If not so, then the interpolation frame creator proceeds to a process for checking for another interpolation method.

At Step S12, a pixel value rk of each interpolation pixel point is determined from the following equation:

$$rk = \sum_{i=1}^{2} (p(t_i) \times w_i)$$

Then, the interpolation frame creating process is returned to Step S9.

According to the ultrasonic diagnostic apparatus 100 of the embodiment 1, the following effects are obtained.

(1) The independent random components rand(1+j+f+d) % Sw−Sw/2 and rand(2+j+f+d) % Sw−Sw/2 are respectively added to the pixel values p(t1) and pt(t2) of the respective pixel points corresponding to the interpolation pixel points on the actual frames F(t1) and F(t2) that interpose the interpolation frames H1, H2 and H3 therebetween, without adding the random components to the calculated pixel values and setting the same as the pixel values of the pixel points on the interpolation frames H1, H2 and H3 thereby to obtain the random-processed pixel values. Thereafter, the pixel value obtained by weighting/adding the random-processed pixel values is used as the pixel value rk. Therefore, the degree of freedom of the added random components reaches 2 and the natural-looking degree can hence be enhanced. For example, sound rays become almost invisible. Regularity between the interpolation frames H1, H2 and H3 becomes unnoticeable.

(2) Although the actual frame may be a color flow image, a B flow image or a B-mode image, the color flow image is useful in particular. That is, when small color data (low in luminance and small in area, for example) buried in the B-mode image of the background and unobtrusive exists in the color flow image, the color data changes with the random components contained therein in the case of each interpolation frame. Therefore, the color data becomes prominent when seen as a moving image, and the existence of the bloodstream becomes easy to recognize visually.

(3) Since it is possible to control the strength of randomness, the appearance of regularity can be optimally suppressed.

In an embodiment 2, spatial interpolation is done on actual frames F(t1) and F(t2) to produce interpolation pixel points, thereby increasing pixel points on the actual frames F(t1) and F(t2). Using the actual frames F(t1) and F(t2) increased in the number of the pixel points makes it possible to enhance interpolation pixel point densities at interpolation frames H1, H2 and H3.

Figure 4:
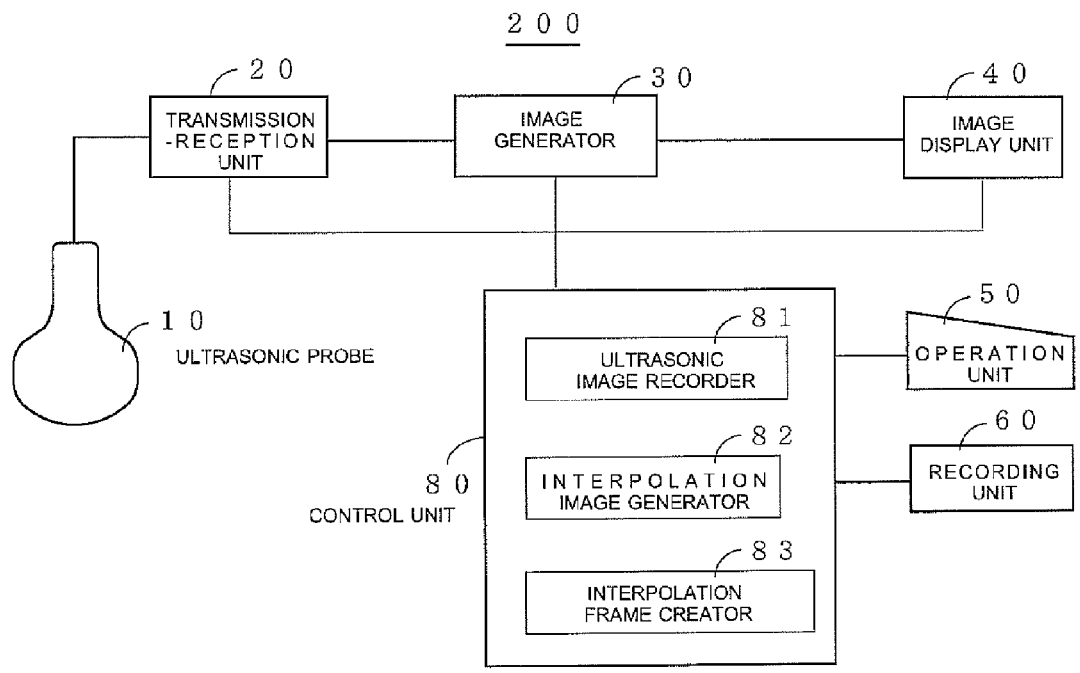
FIG. 4 is a block diagram showing a second exemplary ultrasonic diagnostic apparatus.

FIG. 4 is a construction block diagram of an ultrasonic diagnostic apparatus 200 according to the embodiment 2.

The ultrasonic diagnostic apparatus 200 includes an ultrasonic probe 10, a transmission-reception unit 20 which drives the ultrasonic probe 10 to scan within a subject with an ultrasonic beam, an image generator 30 which generates a time series of ultrasonic images, based on a signal obtained by the transmission-reception unit 20, an image display unit 40 which displays the ultrasonic image and an interpolation image or the like produced based on it, an operation unit 50 for giving instructions and data by an operator, a recording unit 60 which records the ultrasonic image or the like therein, a control unit 80 which controls the whole, and an ultrasonic image recorder 81, an interpolation image generator 82 and an interpolation frame creator 83 both included in the control unit 80.

Figure 5:
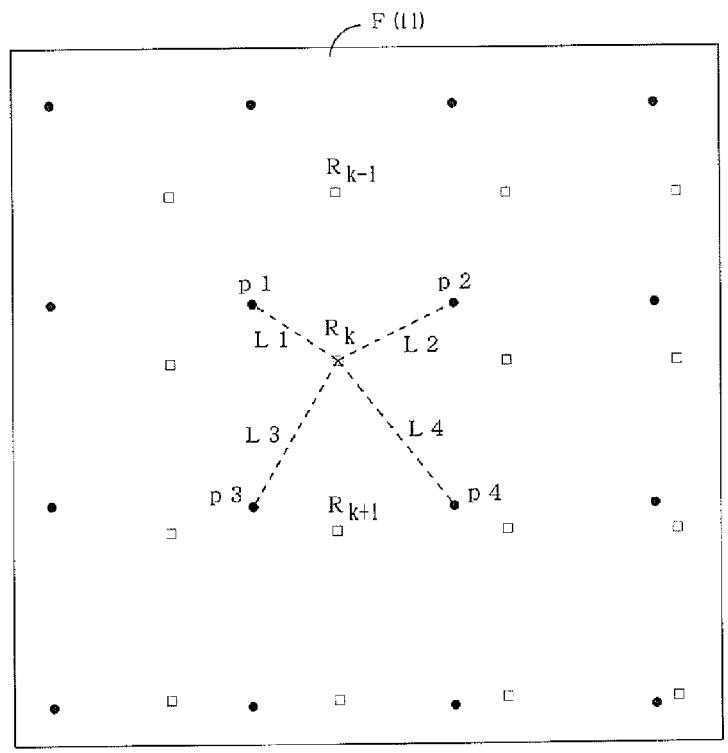
FIG. 5 is a conceptual diagram showing original pixel points and an interpolation pixel point.

FIG. 5 is an explanatory diagram showing original pixel points (pixel points obtained by scanning) and an interpolation pixel point (pixel point obtained by calculations based on the original pixel points).

Original pixel points p1, p2, p3 and p4 are pixel points at which pixel values are obtained by scanning. An interpolation pixel point Rk is a pixel point at which a pixel value is obtained by calculations based on the closest four original pixel points p1, p2, p3 and p4.

FIG. 6 is a flowchart showing an interpolation image generating process executed by the interpolation image generator 82. Incidentally, it will be explained assuming that spatial interpolation is carried out on an actual frame F(t1).

At Step P1, an interpolation pixel point number counter k is initialized to k=1. Interpolation pixel point numbers are serial numbers attached to respective interpolation pixel points on actual frames.

At Step P2 as shown in FIG. 5, the pixel values p1, p2, p3 and p4 of the shortest four original pixel points and distances L1, L2, L3 and L4 are acquired from the position of a kth interpolation pixel point Rk.

At Step P3, the interpolation image generating process proceeds to Step P4 if an operator selects random interpolation. If not so, then the interpolation image generating process proceeds to Step P11.

At Step P4, the interpolation image generating process proceeds to Step P5 if the position of the interpolation pixel point Rk is placed in the neighborhood of a turn-back or return region. If not so, then the interpolation image generating process proceeds to Step P6.

Assuming that the pixel value takes values lying within a range from −128 to 127, for example, the position is determined to be in the vicinity of the return region where |p1-p2|>127, |p3-p4|>127 or |p1-p3|>127 is satisfied.

At Step P5, a standard value So is defined as So=S1. Then, the interpolation image generating process proceeds to Step P7.

At Step P6, the standard value So is defined as So=S2. However, S1 and S2 are assumed to be S1>S2. Then, the interpolation image generating process proceeds to Step P7.

At Step P7, a designated or specified value Sw of random strength is calculated from the following equation:

$$Sw = So + C(\max\{p1,p2,p3,p4\} - \min(p1,p2,p3,p4))$$

where So is a standard value, is an adjustment coefficient, max(p1,p2,p3,p4) is a function that returns the maximum value of p1, p2, p3, and p4, and min(p1,p2,p3,p4) is a function that returns the minimum value of p1, p2, p3, and p4.

At Step P8, a pixel value Rk of each interpolation pixel point is determined from the following equation:

$$Rk = \sum_{i=1}^{4} (p_i + rand(i + j + f + d)\%Sw - Sw/2) \times w_i$$

where pi is a pixel value of each original pixel point close to i-th from interpolation pixel point, rand(seed) is a function that returns pseudorandom numbers based on value of seed, j=0 or j=k, f is zero, a frame number or a sum of a plurality of pixel values of original image, d=0 or is a difference between sum of a plurality of pixel values of original image of present frame and sum of a plurality of pixel values of original image of previous frame, A % B is a function that returns the surplus obtained by dividing A by B, Sw is a designated value of random strength, and wi is a weighting/adding weight.

Here, the operator can select j=0 or j=k. The operator can select either f=0 or the sum of pixel values in the whole surface or partial region on f=frame number or f=actual frame. The operator is able to select the difference between the sum of pixel values in the whole surface or partial region on d=0 or d=actual frame and the sum of pixel values in the whole surface or partial region on the immediately preceding actual frame. A weighting/adding weight wi is calculated from the following equation:

$$w_i = \frac{L_1 * L_2 * L_3 * L_4}{L_i(L_2 * L_3 * L_4 + L_1 * L_3 * L_4 + L_1 * L_2 * L_4 + L_1 * L_2 * L_3)}$$

where Li is a distance from interpolation pixel point to original pixel point close to i-th.

At Step P9, the interpolation image generating process is terminated when the interpolation pixel point number counter k has reached the final value K. If not so, then the interpolation image generating process proceeds to Step P10.

At Step P10, the interpolation pixel point number counter k is incremented by 1 and the interpolation image generating process is returned to Step P2.

At Step P11, the interpolation image generating process proceeds to Step P12 when the operator has selected linear interpolation. If not so, then the interpolation image generating proceeds to a process for checking for another interpolation method.

At Step P12, a pixel value Rk of each interpolation pixel point is determined from the following equation:

$$Rk = \sum_{i=1}^{4} (p_i) \times w_i$$

Then, the interpolation image generating process is returned to Step P9.

Although the interpolation frame creator 83 creates the interpolation frames H1, H2 and H3 using the actual frames F(t1) and F(t2) increased in the number of pixel points by the interpolation image generating process of FIG. 6, the interpolation frame creating process is similar to FIG. 3 and its description will therefore be omitted.

According to the ultrasonic diagnostic apparatus 200 of the embodiment 2, the following effects are obtained in addition to the effects of the embodiment 1.

(4) The spatial interpolation is carried out on the actual frames F(t1) and F(t2) to produce the interpolation pixel points, thereby increasing the pixel points on the actual frames F(t1) and F(t2). It is therefore possible to enhance interpolation pixel point densities at the interpolation frames H1, H2 and H3.

(5) Upon the spatial interpolation on the actual frames F(t1) and F(t2), the different random components rand(1+j+f+d) % Sw−Sw/2, rand(2+j+f+d) % Sw−Sw/2, rand(3+j+f+d) % Sw−Sw/2, and rand(4+j+f+d) % Sw−Sw/2 are respectively added to the pixel values p1, p2, p3 and p4 of the four original pixel points without adding the random components to the calculated pixel values and setting the same as the pixel values of the interpolation pixel points thereby to obtain the random-processed original pixel values. Thereafter, the pixel value obtained by weighting/adding the four random-processed original pixel values is defined as the pixel value Rk corresponding to the interpolation pixel points. Therefore, the degree of freedom of the added random components becomes 4 and the natural-looking degree can hence be enhanced. For example, sound rays become almost invisible. Although the original image may be a color flow image, a B flow image or a B-mode image, the color flow image is useful in particular.

(6) It is possible to define random components different every interpolation pixel point as j=k, define random components different every frame as either f=frame number or the sum of all pixel values in actual frames, and define random components different every frame as the difference between the sum of all pixel values in d=actual frame and the sum of all pixel value in the immediately preceding actual frame. Therefore, the appearance of regular patterns on each actual frame can be suppressed, and the degree that the actual frame is naturally seen can be enhanced.

Many widely different embodiments of the invention maybe configured without departing from the spirit and the scope of the present invention. It should be understood that the present invention is not limited to the specific embodiments described in the specification, except as defined in the appended claims.

What is claimed is:

1. An image processing apparatus comprising:
   a random processing device configured to add independent random components to a pixel value of a pixel point on each actual frame corresponding to a given first time and a pixel value of a pixel point on each actual frame corresponding to a second time subsequent to the first time respectively to obtain random-processed pixel values, wherein the added independent random components have at least two degrees of freedom; and
   a weighting/adding device configured to weight the random-processed pixel values to obtain a pixel value of a pixel point on at least one interpolation frame corresponding to an intermediate time between the first time and the second time, wherein a pixel value rk (where k=1, 2, 3, . . . , K) of each interpolation pixel point is determined from the following equation:

$$rk = \sum_{i=1}^{2} (p(t_i) + rand(i) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i) is a function that returns pseudorandom numbers based on a value of i, rand(i) % Sw is a function that returns the surplus obtained by dividing rand(i) by Sw, Sw is a designated value of random strength, and wi is a weighting/adding weight.

2. The image processing apparatus according to claim 1, including a device which determines a designated value Sw of random strength from the following equation:

$$Sw = So + C(\max\{p(t1), p(t2)\} - \min\{p(t1), p(t2)\})$$

where So is a standard value, C is an adjustment coefficient, max(p(tl),p(t2)) is a function that returns the maximum value of p(t1) and p(t2), and min(p(tl),p(t2)) is a function that returns the minimum value of p(t1) and p(t2).

3. The image processing apparatus according to claim 1, including a weight calculating device which determines a weighting/adding weight wi from the following equation:

$$w_1 = \frac{Tb}{Ta+Tb} \quad w_2 = \frac{Ta}{Ta+Tb}$$

where Ta is a time difference between actual frame immediately before interpolation frame and interpolation frame, and Tb is a time difference between actual frame immediately after interpolation frame and interpolation frame.

4. An image processing apparatus comprising:
   a random processing device configured to add independent random components to a pixel value of a pixel point on each actual frame corresponding to a given first time and a pixel value of a pixel point on each actual frame corresponding to a second time subsequent to the first time respectively to obtain random-processed pixel values, wherein the added independent random components have at least two degrees of freedom; and a weighting/adding device configured to weight the random-processed pixel values to obtain a pixel value of a pixel point on at least one interpolation frame corresponding to an intermediate time between the first time and the second time wherein a pixel value rk (where k=1, 2, 3, ..., K) of each interpolation pixel point is determined from the following equation:

$$rk = \sum_{i=1}^{2}(p(t_i) + rand(i+k)\%Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i+k) is a function that returns pseudorandom numbers based on a value of i+k, rand (i+k) % Sw is a function that returns the surplus obtained by dividing rand(i+k) by Sw, Sw is a designated value of random strength, and wi is a weighting/adding weight.

5. An image processing apparatus comprising:
a random processing device configured to add independent random components to a pixel value of a pixel point on each actual frame corresponding to a given first time and a pixel value of a pixel point on each actual frame corresponding to a second time subsequent to the first time respectively to obtain random-processed pixel values, wherein the added independent random components have at least two degrees of freedom; and
a weighting/adding device configured to weight the random-processed pixel values to obtain a pixel value of a pixel point on at least one interpolation frame corresponding to an intermediate time between the first time and the second time, wherein a pixel value rk (where k=1, 2, 3, ..., K) of each interpolation pixel point is determined from the following equation:

$$rk = \sum_{i=1}^{2}(p(t_i) + rand(i+f)\%Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i+f) is a function that returns pseudorandom numbers based on a value of i+f, f is a serial number of each interpolation frame or sum of pixel values of a plurality of pixel points on each actual frame immediately before or immediately after each interpolation frame, rand(i+f) % Sw is a function that returns the surplus obtained by dividing rand(i+f) by Sw, Sw is a designated value of random strength, and wi is a weighting/adding weight.

6. An image processing apparatus comprising:
a random processing device configured to add independent random components to a pixel value of a pixel point on each actual frame corresponding to a given first time and a pixel value of a pixel point on each actual frame corresponding to a second time subsequent to the first time respectively to obtain random-processed pixel values, wherein the added independent random components have at least two degrees of freedom; and a weighting/adding device configured to weight the random-processed pixel values to obtain a pixel value of a pixel point on at least one interpolation frame corresponding to an intermediate time between the first time and the second time, wherein a pixel value rk (where k=1, 2, 3, ..., K) of each interpolation pixel point is determined from the following equation:

$$rk = \sum_{i=1}^{2}(p(t_i) + rand(i+d)\%Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i+d) is a function that returns pseudorandom numbers based on a value of i+d, d is a difference between sum of pixel values of a plurality of pixel points on each actual frame immediately before each interpolation frame and sum of pixel values of a plurality of pixel points on each actual frame immediately after each interpolation frame, rand(i+d) % Sw is a function that returns the surplus obtained by dividing rand(i+d) by Sw, Sw is a designated value of random strength, and wi is a weighting/adding weight.

7. An image processing apparatus comprising:
a random processing device configured to add independent random components to a pixel value of a pixel point on each actual frame corresponding to a given first time and a pixel value of a pixel point on each actual frame corresponding to a second time subsequent to the first time respectively to obtain random-processed pixel values, wherein the added independent random components have at least two degrees of freedom; and
a weighting/adding device configured to weight the random-processed pixel values to obtain a pixel value of a pixel point on at least one interpolation frame corresponding to an intermediate time between the first time and the second time, wherein a pixel value rk (where k=1, 2, 3, ..., K) of each interpolation pixel point is determined from the following equation:

$$rk = \sum_{i=1}^{2}(p(t_i) + rand(i+j-f+d)\%Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i+j+f+d) is a function that returns pseudorandom numbers based on a value of i+j+f+d, j is equal to one of zero and k, f is one of a value equal to zero and a sum of pixel values of a plurality of pixel points on serial number of each interpolation frame or each actual frame immediately before or immediately after each interpolation frame, d is one of a value equal to zero and a difference between sum of pixel values of a plurality of pixel points on each actual frame immediately before each interpolation frame and sum of pixel values of a plurality of pixel points on each actual frame immediately after each interpolation frame, and rand(i+j+f+d) % Sw is a function that returns the surplus obtained by dividing rand(i+j+f+d) by Sw.

8. An ultrasonic diagnostic apparatus comprising:
an ultrasonic scan device configured to scan a subject by ultrasound to obtain time-series actual frames;
a random processing device configured to add independent random components to a pixel value of a pixel point on each actual frame corresponding to a first given time and a pixel value of each original pixel point on each actual frame corresponding to a second time subsequent to the first time respectively to obtain random-processed pixel values, wherein the added independent random components have at least two degrees of freedom;
a weighting/adding device configured to weight the random-processed pixel values to obtain a pixel value of a pixel point on at least one interpolation frame corresponding to an intermediate time; and
an image display device configured to display the at least one interpolation frame, wherein a pixel value rk (where k=1, 2, 3, . . . , K) of each interpolation pixel point is determined from the following equation:

$$rk = \sum_{i=1}^{2} (p(t_i) + rand(i) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i) is a function that returns pseudorandom numbers based on a value of i, rand(i) % Sw is a function that returns the surplus obtained by dividing rand(i) by Sw, Sw is a designated value of random strength, and wi is a weighting/adding weight.

9. The ultrasonic diagnostic apparatus according to claim 8, further comprising a first device configured to determine whether the position of each interpolation pixel point is in the neighborhood of a turn-back region, and a second device configured to determine the designated value Sw of random strength in such a manner that the designated value Sw becomes greater than that at other position at the position in the neighborhood of the turn-back region.

10. An ultrasonic diagnostic apparatus comprising:
an ultrasonic scan device configured to scan a subject by ultrasound to obtain time-series actual frames;
a random processing device configured to add independent random components to a pixel value of a pixel point on each actual frame corresponding to a first given time and a pixel value of each original pixel point on each actual frame corresponding to a second time subsequent to the first time respectively to obtain random-processed pixel values, wherein the added independent random components have at least two degrees of freedom;
a weighting/adding device configured to weight the random-processed pixel values to obtain a pixel value of a pixel point on at least one interpolation frame corresponding to an intermediate time; and
an image display device configured to display the at least one interpolation frame, wherein a pixel value rk (where k=1, 2, 3, . . . , K) of each interpolation pixel point is determined from the following equation:

$$rk = \sum_{i=1}^{2} (p(t_i) + rand(i+k) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point a actual frame immediately after interpolation frame, rand(i+k) is a function that returns pseudorandom numbers based on a value of i+k, rand (i+k) % Sw is a function that returns the surplus obtained by dividing rand(i+k) by Sw, Sw is a designated value of random strength, and wi is a weighting/adding weight.

11. The ultrasonic diagnostic apparatus according to claim 10, further comprising a first device configured to determine whether the position of said each interpolation pixel point is in the neighborhood of a turn-back region, and a second device configured to determine the designated value Sw of random strength in such a manner that the designated value Sw becomes greater than that at other position at the position in the neighborhood of the turn-back region.

12. An ultrasonic diagnostic apparatus comprising:
an ultrasonic scan device configured to scan a subject by ultrasound to obtain time-series actual frames;
a random processing device configured to add independent random components to a pixel value of a pixel point on each actual frame corresponding to a first given time and a pixel value of each original pixel point on each actual frame corresponding to a second time subsequent to the first time respectively to obtain random-processed pixel values, wherein the added independent random components have at least two degrees of freedom;
a weighting/adding device configured to weight the random-processed pixel values to obtain a pixel value of a pixel point on at least one interpolation frame corresponding to an intermediate time; and
an image display device configured to display the at least one interpolation frame, wherein a pixel value rk (where k=1, 2, 3, . . . , K) of each interpolation pixel point is determined from the following equation:

$$rk = \sum_{i=1}^{2} (p(t_i) + rand(i+f) \% Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i+f) is a function that returns pseudorandom numbers based on a value of i+f, f is one of a serial number of each interpolation frame and a sum of pixel values of a plurality of pixel points on each actual frame immediately before or immediately after each interpolation frame, rand(i+f) % Sw is a function that returns the surplus obtained by dividing rand(i+f) by Sw, Sw is a designated value of random strength, and wi is a weighting/adding weight.

13. The ultrasonic diagnostic apparatus according to claim 12, further comprising a first device configured to determine whether the position of said each interpolation pixel point is in the neighborhood of a turn-back region, and a second device configured to determine the designated value Sw of random strength in such a manner that the designated value Sw becomes greater than that at other position at the position in the neighborhood of the turn-back region.

14. An ultrasonic diagnostic apparatus comprising:
an ultrasonic scan device configured to scan a subject by ultrasound to obtain time-series actual frames;
a random processing device configured to add independent random components to a pixel value of a pixel point on each actual frame corresponding to a first given time and a pixel value of each original pixel point on each actual frame corresponding to a second time subsequent to the first time respectively to obtain random-processed pixel values, wherein the added independent random components have at least two degrees of freedom;
a weighting/adding device configured to weight the random-processed pixel values to obtain a pixel value of a pixel point on at least one interpolation frame corresponding to an intermediate time; and
an image display device configured to display the at least one interpolation frame, wherein a pixel value rk (where k=1, 2, 3, . . . , K) of each interpolation pixel point is determined from the following equation:

$$rk = \sum_{i=1}^{2} (p(t_i) + rand(i+d)\%Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i+d) is a function that returns pseudorandom numbers based on value of i+d, d is a difference between sum of pixel values of a plurality of pixel points on each actual frame immediately before each interpolation frame and sum of pixel values of a plurality of pixel points on each actual frame immediately after each interpolation frame, rand(i+d) % Sw is a function that returns the surplus obtained by dividing rand(i+d) by Sw, Sw is a designated value of random strength, and wi is a weighting/adding weight.

15. An ultrasonic diagnostic apparatus comprising:
an ultrasonic scan device configured to scan a subject by ultrasound to obtain time-series actual frames;
a random processing device configured to add independent random components to a pixel value of a pixel point on each actual frame corresponding to a first given time and a pixel value of each original pixel point on each actual frame corresponding to a second time subsequent to the first time respectively to obtain random-processed pixel values, wherein the added independent random components have at least two degrees of freedom;
a weighting/adding device configured to weight the random-processed pixel values to obtain a pixel value of a pixel point on at least one interpolation frame corresponding to an intermediate time; and
an image display device configured to display the at least one interpolation frame, wherein a pixel value rk (where k=1, 2, 3, . . . , K) of each interpolation pixel point is determined from the following equation:

$$rk = \sum_{i=1}^{2} (p(t_i) + rand(i+j+f+d)\%Sw - Sw/2) \times w_i$$

where p(t1) is a pixel value of pixel point corresponding to interpolation pixel point at actual frame immediately before interpolation frame, p(t2) is a pixel value of pixel point corresponding to interpolation pixel point at actual frame immediately after interpolation frame, rand(i+j+f+d) is a function that returns pseudorandom numbers based on value of i+j+f+d, j is equal to one of zero and k, f is one of a value equal to zero and a sum of pixel values of a plurality of pixel points on serial number of each interpolation frame or each actual frame immediately before or immediately after each interpolation frame, d is one of a value equal to zero and a difference between sum of pixel values of a plurality of pixel points on each actual frame immediately before each interpolation frame and sum of pixel values of a plurality of pixel points on each actual frame immediately after each interpolation frame, and rand(i+j+f+d) % Sw is a function that returns the surplus obtained by dividing rand(i+j+f+d) by Sw.

16. An ultrasonic diagnostic apparatus including comprising:
an ultrasonic scan device configured to scan a subject by ultrasound to obtain time-series actual frames;
a random processing device configured to add independent random components to a pixel value of a pixel point on each actual frame corresponding to a first given time and a pixel value of each original pixel point on each actual frame corresponding to a second time subsequent to the first time respectively to obtain random-processed pixel values, wherein the added independent random components have at least two degrees of freedom;
a weighting/adding device configured to weight the random-processed pixel values to obtain a pixel value of a pixel point on at least one interpolation frame corresponding to an intermediate time;
an image display device configured to display the at least one interpolation frame; and
a device which determines a designated value Sw of random strength from the following equation:

$$Sw = So + C(\max\{p(t1), p(t2)\} - \min\{p(t1), p(t2)\})$$

where So is a standard value, C is an adjustment coefficient, max(p(t1),p(t2)) is a function that returns the maximum value of p(t1) and p(t2), and min(p(t1),p(t2)) is a function that returns the minimum value of p(t1) and p(t2).

17. An ultrasonic diagnostic apparatus comprising:
an ultrasonic scan device configured to scan a subject by ultrasound to obtain time-series actual frames;
a random processing device configured to add independent random components to a pixel value of a pixel point on each actual frame corresponding to a first given time and a pixel value of each original pixel point on each actual frame corresponding to a second time subsequent to the first time respectively to obtain random-processed pixel values, wherein the added independent random components have at least two degrees of freedom;
a weighting/adding device configured to weight the random-processed pixel values to obtain a pixel value of a pixel point on at least one interpolation frame corresponding to an intermediate time;
an image display device configured to display the at least one interpolation frame; and a device configured to determine a weighting/adding weight wi from the following equation:

$$w_1 = \frac{Tb}{Ta+Tb} \quad w_2 = \frac{Ta}{Ta+Tb} \quad\quad 5$$

where Ta is a time difference between actual frame immediately before interpolation frame and interpolation frame, and Tb is a time difference between actual frame immediately after interpolation frame and interpolation frame.

* * * * *

UNITED STATES PATENT AND TRADEMARK OFFICE
CERTIFICATE OF CORRECTION

| | |
|---|---|
| PATENT NO. | : 8,096,950 B2 |
| APPLICATION NO. | : 12/188112 |
| DATED | : January 17, 2012 |
| INVENTOR(S) | : Tanigawa et al. |

It is certified that error appears in the above-identified patent and that said Letters Patent is hereby corrected as shown below:

In Column 8, Line 14, delete "oil" and insert -- on --, therefor.

In Column 10, Line 63, delete "HI" and insert -- H1 --, therefor.

In Column 12, Line 59, delete "$(p(t_i)$" and insert -- $(p(t_i))$ --, therefor.

In Column 16, Line 44, in Claim 2, delete "max(p(tl),p(t2))" and insert -- max(p(t1),p(t2)) --, therefor.

In Column 16, Line 45, in Claim 2, delete "min(p(tl),p(t2))" and insert -- min(p(t1),p(t2)) --, therefor.

In Column 17, Line 5, in Claim 4, delete "time" and insert -- time, --, therefor.

In Column 18, Lines 47-48, in Claim 7, delete "(i+j-f+d)" and insert -- (i+j+f+d) --, therefor.

Signed and Sealed this
Eighteenth Day of September, 2012

David J. Kappos
*Director of the United States Patent and Trademark Office*